United States Patent [19]

Li

[11] Patent Number: 6,117,846

[45] Date of Patent: Sep. 12, 2000

[54] NUCLEIC ACID FILTERS

[76] Inventor: Yin-Xiong Li, Medical College of Georgia, Dept. of Immunology & Microbiology, RE Building 2607, Augusta, Ga. 30912-2400

[21] Appl. No.: 08/939,858

[22] Filed: Sep. 29, 1997

Related U.S. Application Data

[63] Continuation of application No. 08/272,096, Jul. 8, 1994, abandoned.

[51] Int. Cl.$^7$ .............................. A61K 7/42; A61K 31/70; C07H 21/04; A01N 43/04
[52] U.S. Cl. ............................... 514/44; 536/23.1; 424/59
[58] Field of Search ............................. 514/44; 536/23.1; 424/59

[56] References Cited

U.S. PATENT DOCUMENTS

| | | | |
|---|---|---|---|
| 3,892,844 | 7/1975 | Erlemann | 424/59 |
| 3,937,809 | 2/1976 | Jacobi | 514/47 |
| 4,464,362 | 8/1984 | Kludas | 424/114 |
| 5,066,082 | 11/1991 | Longstaff | 359/361 |
| 5,470,577 | 11/1995 | Gilchrest et al. | 424/450 |

FOREIGN PATENT DOCUMENTS

WO 95/10773   1/1995   WIPO .

OTHER PUBLICATIONS

Ananthaswamy and Pierceall, *Photochem and Photobiol.*, 52(6):1118–1136, 1990.
Castleman, *Mother Jones*, May–Jun. 1993, pp. 33–37.
Chiang and Rupert, *Photochem. Photobiol.*, 30:525–528, 1979.
Consumer Reports, Jun. 1991, p. 406.
Coohill, *Photochemistry and Photobio.*, 54:859–870, 1991.
Fisher, AA, *Arch. Dermatol.*, 113:1288–1300, 1977.
Gurish, *J. Invest. Dermatol.*, 76:246–251, 1981.
Hanawalt and Haynes, *Scientific American*, 216:36, 1967.
Henriksen T., *Photochem. Photobiol.*, 51(5): 579–82, 1990.
Ishiura et.al., *Mol. Cell. Biol.* 2:607–616, 1982.
Kaidbey, *J. Soc. Cosmet. Chem.* 29:525–536, 1978.
Kelfkens G., *Photochem. Photobiol.*, 52(4):819–23, 1990.
Knowland, *FEBS Letters*, 324:308–313, 1993.

Laird, P., *Nucleic Acids Reasearch*, 19:4293, 1991.
Mathias, *Arch Dermatol.*, 114:1665–1666, 1978.
Matsuoka, *Arch. Dermatol.* 124:1802–1804, 1988.
Moan, J., *Br. J. Cancer*, 65:916–921, 1992.
Preston, *New England J. Med.*, 327:1649–1662, 1992.
Rupert, C.S., *J.Gen.Physiol.* 45:725–741, 1962.
Thompson, *The New England J. of Med.*, 329:1147–1151, 1993.
Young, *British J. of Dermatology*, 122, Supplement 35:111–114, 1990.
Young, *Pigment Cell Research*, 1:350–4, 1988.
Dumaz et al., *Proc. Natl. Acad. Sci.*, 1993, 90:10529–10533.
Garland, et al., *Health*, 1992, 82: –, No. 4.
Hanawalt, et al., *Scientific American*, 1967, 216:36.
Hilchey, 1993, DNA to be Used to monitor effects of Ozone Depletion.
Jager, et al., *Arch. Dermatol.*, 1977, 113:1288–1289.
Knowland, et al., *FEBS Letters*, 1993, 324:308–313.
Ley et al., *Molecular Studies in Ultraviolet Radiation Carcinobenesis*, "Experimental and Clinical Photoimmunology" Chap. 4, 1:61–68, 19 Year Un–Available.
Pathak, et al., *Protection of Skin against Solar Radiation*, Chap. 15, pp. 441–473, 19 Year Not Available.
Puskeppeleit, et al., *Applied and Enviromental Microbiology*, 1992, 58:2355–2359.
Regan, et al., *Photochemistry and Photobiology*, 1992, 56:35–42.
Rogers, et al., *British Journal of Dermatology*, 1990, 122:55–60.
Sutherland, *Ultraviolet Light–Induced Damage and Its Repair*, "Experimental and Clinical Photoimmunology" 19xx, Chapter 2, vol. 1, pp. 27–38 Year Not Available.
Spikes, J.D., In: Exp. Clin. Photoimmunology, Daynes and Spikes, (eds.), CRC Press, Boca Raton, 1983.
Ghosh, S., Sci. Cult. (1979), 45(11), 450–452.

*Primary Examiner*—Deborah Crouch
*Assistant Examiner*—Anne-Marie Baker
*Attorney, Agent, or Firm*—Merchant & Gould

[57] ABSTRACT

The use of nucleic acid-containing materials, such as deoxyribonucleic acid and ribonucleic acid, as ultraviolet radiation filters for specifically absorbing genetic hazard ultraviolet radiation by the interposition of a nucleic acid-containing barrier between a source of UV radiation and a living organism.

16 Claims, No Drawings

NUCLEIC ACID FILTERS

This is a Continuation of application Ser. No. 08/272,096, filed Jul. 8, 1994, now abandoned.

BACKGROUND OF THE INVENTION

1. Field of the Invention

The present invention relates to the use of nucleic acids such as deoxyribonucleic acid and ribonucleic acid (hereinafter collectively referred to as "NA") as a filter for removing environmental hazards that otherwise would pose a threat to the genetic material of living organisms such as plants and animals, including humans. More particularly, the present invention relates to a method of use of NA as a sunlight or artificial UV light filter to selectively remove nucleic acid-damaging ultraviolet radiation, for example, from sunlight or artificial UV source, before it contacts a living organism. Even more particularly, the present invention relates to NA-containing compositions and articles which form an ultraviolet radiation-absorbing layer between the sun and living organisms where the layer specifically blocks nucleic acid-damaging ultraviolet radiation before it contacts a living organism.

2. Background of the Invention

One of the major causes of cancer is the alteration of the cellular genome. Environmental hazards that specifically react with nucleic acids are a major cause of these genetic alterations, and hence a major cause of cancer in both plants and animals. Typical environmental hazards that have nucleic acid-damaging capabilities include, inter alia, ultraviolet radiation, ionizing radiation, and environmental chemicals that display either nucleic acid intercalating activity or the ability to form adducts with nucleic acids.

Exposure to ultraviolet radiation from the sun is generally believed to be the major cause of non-melanoma skin cancers and a major cause of malignant melanoma skin cancers (Moan and Dahlback, *Br. J. Cancer* 65:916–921, 1992). Rates of both non-melanoma and malignant melanoma skin cancers have increased dramatically in recent years. For example, during the period between 1957 and 1984 in Norway, the incidence of cutaneous malignant melanoma increased by 350% for men and 440% for women. According to a recent U.S. federal survey taken between 1977–1988, about 500,000 basal-cell carcinomas and 100,000 squamous-cell carcinomas occur annually. Other, smaller surveys suggest the incidence may have increased by as much as 65% since 1980. (Preston and Stern, *New England J. Med.*, 327:1649–1662, 1992). Scientists have linked the recent increase in skin cancer with the decrease in the Earth's protective ozone layer, a layer that normally filters out much of the nucleotide damaging ultraviolet radiation in sunlight. As the Earth's protective ozone layer continues to decrease, the earth's surface is exposed to increasingly higher levels of nucleic acid-damaging ultraviolet radiation from the sun. Ozone depletion may seriously impact such important biological end-points as skin cancer, cataracts, the immune system, crop yields, and oceanic phytoplankton (Coohill, *Photochemistry and Photobio.*, 54:859–870, 1991). Scientists believe that this increased irradiation will especially lead to a related increase the incidence of sunlight-induced skin cancer. (Kelfkens G., etc. *Photochem. Photobiol.*, 52(4):819–23, 1990). Henriksen predicted a two percent increase in overall skin cancer for each one percent depletion of stratospheric ozone. (Henriksen T., *Photochem. Photobiol.* 51(5):579–82, 1990).

Currently, in response to the threat of exposure to harmful ultraviolet radiation from the sun, people are advised to avoid excessive exposure to sunlight, and when in the sun, to wear sunscreens. The shortcomings of these actions are many fold, including their limitation to humans, as opposed to all other living creatures, as well as numerous problems inherent in existing sunscreen technology.

A more desired response to the global threat of increased exposure to nucleic acid-damaging ultraviolet radiation would provide protection for all living creatures, not merely humans. The present invention affords such protection.

Existing topical sunscreens fall within one of two categories: (1) chemical, and (2) physical sunscreens. Physical sunscreens operate by blocking out nearly all wavelengths of sunlight (290–760 nm). They are typically applied in an opaque cream or lotion containing particulate ingredients that do not selectively absorb ultraviolet radiation, but when applied as a thin film, primarily reflect and scatter sunlight. Common ingredients in physical sunscreens include titanium dioxide, zinc oxide and talc.

Because they completely block all sunlight, known physical sunscreens prevent the beneficial effects of sunlight upon the skin. For example, physical sunscreens block the wavelengths of sunlight that are essential for the skin to convert 7-dehydro-cholesterol into vitamin $D_3$ (Matsuoka et.al., *Arch. Dermatol.* 124:1802–1804, 1988) and block sunlight required for the photoactivation of a protein called photolyase which is involved in cellular DNA repair mechanism (Rupert, C. S., *J.Gen.Physiol.* 45:725–741, 1962). Physical sunscreens also prevent the often desired "tanning" of the skin which would otherwise occur upon exposure to moderate amounts of sunlight. Further, physical sunscreen formulations are cosmetically unpleasing, unacceptable to many patients, and messy to use.

Chemical sunscreens contain one or more ultraviolet-absorbing chemicals which are generally colorless, and upon application of a thin and invisible film, act as filters to selectively prevent certain wavelengths of ultraviolet light from reaching the cells of the epidermis. However, since chemical sunscreens are non-natural molecules, their molecular structures are quite different from the nucleic acid molecules which are the direct target for ultraviolet light-induced damage to living organisms (Ananthaswamy and Pierceall, *Photochem and Photobiol.*, 52(6):1118–1136, 1990). Also, due to a lack of understanding of the photochemistry of nucleic acids, whether or not chemical sunscreens protect living organisms from skin cancer is still an unresolved controversy (Gurish, *J. Invest. Dermatol.*, 76:246–251, 1981; Knowland, *FEBS Letters*, 324:308–313, 1993; Thompson, *The New England J. of Med.*, 328:1147–1151, 1993). Further, the radiation that is blocked out by known chemical sunscreens often includes frequencies of sunlight that are beneficial to the body such as the wavelengths of ultraviolet light that are necessary for the body to produce vitamin D.

Most commercial sunscreens contain at least one each of two different types of chemicals: UV-A-absorbing chemicals and UV-B-absorbing chemicals. UV-A-absorbing chemicals absorb ultraviolet radiation in the range of 320–400 nm. UV-B-absorbing chemicals absorb ultraviolet radiation in the range of 290–320 nm. The wavelength range of UV-A and UV-B (290–400 nm) includes the frequencies of ultraviolet light that cause sunburn (290–350 nm), however, it also includes beneficial wavelengths of ultraviolet light such as those that are necessary for the skin's production of vitamin $D_3$ (290–315 nm) and also those required for repair of pyrimidine dimers (320–600 nm) (Spikes, J. D., In: *Experimental and Clinical Photoimmunology*, Daynes and Spikes (eds.), CRC Press, Boca Raton (1983); Chiang and Rupert, *Photochem. Photobiol.,* 30:525–528, 1979; Hanawalt and Haynes, *Scientific American,* 216:36, 1967).

UV-absorbing chemicals include para-aminobenzoic acid (PABA) and esters thereof, benzophenones, and cinnemates which selectively absorb and screen sunburn-producing UV radiation (290–320 nm). However, sunscreening formulations containing these chemicals can cause selective burning (smarting), contact dermatitis, and allergic contact dermatitis. (Kaidbey et al., *J. Soc. Cosmet. Chem.* 29:525–536, 1978; Fisher, AA, *Arch. Dermatol.,* 113: 1288–1300, 1977; Toby-Mathias et al., *Arch Dermatol.,* 114:1665–1666, 1978). Further, synthetic procedures for producing UV-absorbing chemicals may introduce contaminants into the preparation, some which may be carcinogenic. For example, urocranic acid was commercially available as a sunscreen to block UV-B, but was removed from the market because of its link to skin cancer (*Consumer Reports, June* 1991, p. 406). Chemical sunscreens may mutate on exposure to sunlight, the mutagen being carcinogenic. Indeed, studies suggest that chemical sunscreens might encourage rather than prevent sunlight-related cancers (Knowland et al., *FEBS Letters,* 324:309–313, 1993).

Further, the sun protection factor (SPF) rating used to quantitate protection offered by a commercial sunscreen product is based upon erythema, a morphological criteria that is not directly related to quantitation of genetic hazard protection. The SPF rating may be more harmful than useful. Those who purchase and use a sunscreen with a high SPF expect the sunscreen to protect them from genetic hazard UV radiation. With a false sense of security, they may spend a greater amount of time exposed to UV radiation, while the sunscreen may not provide adequate protection. (Young, *British J. of Dermatology,* 122, Supplement 35:111–114, 1990; Young, *Pigment Cell Research,* 1:350–4, 1988). The SPF rating is not directly related in any way to UV-induced DNA damage. The SPF standard is based upon erythema, or redness caused by UV exposure.

The wavelengths of light absorbed by the various chemical sunscreens differs with the compounds used. Because the specific wavelengths responsible for UV-induced DNA damage are not fully understood, a non-target compound cannot be certain to be an effective filter.

It would be of great utility to provide a natural genetic hazard UV radiation filter which could selectively and specifically eliminate genetic-hazard inducing UV radiation.

SUMMARY OF THE INVENTION

The present invention describes a method wherein nucleic acids are used to selectively remove nucleic acid-damaging hazards from the environment before those hazards would otherwise reach and potentially harm plants and animals, including humans.

In the preferred embodiment of the invention, NA is used to selectively absorb, and thereby remove, nucleic acid-damaging ultraviolet radiation from artificial sources or from sunlight. Generally, in the preferred embodiment, a layer of NA-containing material is interposed between a living organism and the UV source the NA-containing material may be, for example, a cream applied to the surface of a target; a fabric sheet worn as clothing by the target, or a shield protecting a larger habitat. Generally, this NA-containing barrier contains a sufficient amount of nucleic acid to selectively absorb and filter genetic hazard ultraviolet radiation and thereby shield a target from nucleic acid-damaging radiation. This NA-containing barrier generally consists of, for example, NA in or on a transparent surface, in or on a solid matrix, a NA coated fiber which may or may not be woven, a composition for topical application of an NA-containing mixture, or other suitable means of placing an NA-containing barrier between a UV radiation source (sun or artificial UV source) and a living organism. In a preferred embodiment, a NA-containing lotion or cream is applied to a surface such as skin to shield an animal from exposure to damaging ultraviolet radiation.

The preferred embodiment of the present invention overcomes problems presented by physical sunscreens and by chemical sunscreens. Because the nucleic acid filter reacts with ultraviolet radiation in approximately the same way as UV contacts and catalyzes DNA molecules in living organisms, its use as a sunlight filter is clearly superior to existing chemical and physical sunscreens. By using the same target molecules in the filter, the nucleic acid filter provides selective absorption of the specific UV spectra that cause cancer-inducing genetic damage, while allowing other, beneficial wavelengths of sunlight to shine upon epidermal cells.

DETAILED DESCRIPTION

The present invention relates to a method of filtering out or absorbing genetic hazard ultraviolet radiation before it contacts a living organism, particularly nucleic acid-damaging radiation from natural or artificial UV sources, through the use of a nucleic acid-containing filter located between the UV source and a living organism. In the present invention, the term "nucleic acid" (NA) is meant to include DNA and RNA as well as their constituent nucleotides, nucleosides, bases and derivatives thereof, to the extent each of these is able to selectively absorb genetic hazard UV radiation. Derivatives include, for example, alcohol-modified NA due to a shift in its absorbance spectrum toward known genetic hazard wavelengths, may be preferred. The NA may be natural or synthetic, including NA produced by genetic engineering methods. One of skill in the art will recognize many types of NA molecules useful as NA filters in the present invention. To screen for a useful NA molecule, one can prepare a composition of the NA and test its ability to shield a test sample of DNA from UV-induced damage, as compared with a non-shielded control, for example using the tests described in the Examples which follow.

The term "genetic hazard" ultraviolet radiation is meant to include those wavelengths of ultraviolet radiation that induce alterations in genetic materials, particularly in NA, including dimerization of bases.

In a preferred embodiment, the nucleic acids in the NA-barrier are either deoxyribonucleic acid ("DNA") or ribonucleic acid ("RNA"), obtained from animal and plant tissues or by genetic engineering methods. The NA may be present in the NA barrier in any means suitable for providing a layer of NA between the UV source and a living organism. The barrier may be a coating composition suitable for coating the surface of an inert substance with an even layer of NA sufficient to absorb genetic hazard ultraviolet radiation. This barrier film of NA may be in a cream for topical application to the skin, in or on an inert surface or shield, in or on a solid matrix, or in or on a fiber which may or may not be woven.

The amount of NA needed to provide the desired protection will vary with the nature of the barrier, the source and intensity of the radiation and other well recognized variables. Suitable amounts can be readily determined by standard methods of testing, for example, by the methods outlined in the Examples. NA is generally incorporated in the barrier in an amount ranging from about 15 $\mu$g/cm$^2$ to about 150 $\mu$g/cm$^2$, preferably at least about 50 $\mu$g/cm$^2$.

For surface application, carriers include any vehicle or medium capable of incorporating the NA ultraviolet filter compound in a manner permitting uniform application to the surface. For topical application on skin, the carrier must be pharmaceutically acceptable. The term "pharmaceutically acceptable" is intended to mean the carrier is dermatologically acceptable. The carrier may comprise a wax, oil or cream base material in which NA can be held in a clear solution or a uniform dispersion, for example, as submicron size particles. Preferably the carrier comprises a suitable solvent or a mixture of solvents capable of solubilizing the NA to provide a concentration that is effective as a UV light filtering agent when incorporated in the formulation. Solvents that may be useful include water, alcohols, ketones, esters, polyesters, such as oils, hydrocarbons, ethers, polyethers, polyetherpolyols, and other special solvents such as dimethylsulfoxide, dimethylformamide, dimethylisosoribide, and the like. Some of the above-named ingredients are not pharmaceutically acceptable, but are useful in other applications.

The topical compositions may be applied as a liquid or as a lotion or cream comprising a water-in-oil, an oil-in-water or a multiple emulsion. The topical compositions will form a continuous film of genetic hazard ultraviolet radiation-filtering NA. Such film may also contain other ultraviolet absorbing chemicals, such as UV-A-absorbing and UV-B-absorbing chemicals to provide protection against sunburn. Because the UV filters are often used in hot weather and in conjunction with water-related activities, it is desirable that the protective coating applied to the skin not be appreciably affected by water or perspiration.

In addition to its application to surfaces in the form of lotions and creams, NA may also be directly applied to inert surfaces. For example, the NA may be directly annealed to plastic and to solid matrices as described more fully in the examples below.

The UV-absorbing compositions and articles of the present invention are useful as specific genetic hazard UV radiation-absorbing barriers or shields when placed between a target and a source of UV radiation. The precise location of the barrier or shield will vary, e.g., creams applied directly to the skin and insert substances as habitat shields positioned a large distance from the target. However, the placement of the barrier or shield is in the path from UV source to target, thus providing a genetic-hazard UV radiation absorbing barrier preventing the UV radiation from contacting the target.

Because the compositions of the present invention include the molecules which are a natural target for genetic-hazard UV radiation, they form a specific barrier which will absorb genetic-hazard UV radiation at whatever wavelengths, known or unknown, which cause damage. These compositions thus provide a uniquely specific barrier.

The following examples serve as non-limiting illustrations of the types of compounds and methods used in the invention. The following examples serve to illustrate, but not to limit the practice of the invention.

EXAMPLES

Example 1

Representative Procedures for Preparation of Nucleic Acid from Animal Tissue A. Preparation of Genomic DNA-Method I Five volumes of homogenizing solution consisting of 10 mM Tris[Hydroxylmethyl] aminomethane hydrochloride (Tris.Cl) pH7.4, 10 mM NaCl, 25 mM ethylene diaminetetraacitic acid (EDTA), and 0.5% sodium dodecyl sulfate (SDS), was added to one volume of fresh porcine liver which had been cut into small pieces. The resulting mixture was homogenized to break the cell membranes. The homogenate was centrifuged for 5 min at 2500×relative centrifugal force (RCF). Then, 3 volumes of an extraction buffer consisting of 10 mM Tris.Cl pH8.0, 0.1 M EDTA, pH8.0, 20 ug/ml pancreatic RNase, and 0.5% SDS, were added to the supernatant. Proteinase K was then added to a final concentration of 100 ug/ml, by gently mixing the enzyme into the solution with a glass rod. The lysate was then incubated in a water bath for 3 hours at 50° C. with occasional stirring. Following the 3 hour incubation, an equal volume of phenol, equilibrated with o.5M Tris Cl, pH8.0, was added to the solution. The two phases were mixed by stirring for 10 minutes. The phases were separated by centrifugation at 5000×RCF, for 15 minutes at room temperature. The aqueous phases were transferred to a clean centrifuge tube. The extraction was then repeated two more times with equal volume of phenol-chloroform, isoamyl alcohol (25:24:1) and equal volume of chloroform. After the third extraction, the aqueous phases were mixed with 0.1 volume of 3M NaAc (pH 7.0) and 2 volumes of ethanol (95%), centrifuged for 20 minutes at 10,000 RCF and the resulting DNA pellet was washed with 75% ethanol and then redissolved with a Tris-EDTA buffer consisting of 10 mM Tris.Cl pH8.0, and 1 mM EDTA pH8.0.

The resulting high molecular weight genomic DNA was then digested with DNase I to generate DNA fragments sized approximately smaller than 5 Kb. The DNA fragments were extracted with phenol-chloroform and ethanol precipitation. The DNA pellet was dissolved in TE buffers (pH 8.0). The absorbance of the DNA at 260 nm and 280 nm was measured and the ratio of $A_{260}$ to $A_{280}$ was 1.8. The DNA concentration was calculated based on $OD_{260}$ (1 $OD_{260}$=50 ug/ml DNA).

B. Preparation of Genomic DNA-Method II

One gram of fresh porcine liver that had been cut into small pieces was mixed with 20 ml of a lysate solution consisting of 5M Guanidine thiocyanate and 0.01M EDTA, pH 8.0. The resulting mixture was then homogenized in a blender. Glass particles of between 5 μm and 25 μm diameter were added to the homogenate to a final concentration of 5% in a glass particle-DNA binding buffer consisting of 6M sodium perchlorate, 50 mM Tris.Cl, pH 8.0, and 10 mM Trans-1, 2-diaminocyclohexane-N,N,N',N'-tetraacetic acid (TDTA). The resulting mixture was agitated at room temperature for 20 minutes and then centrifuged at 5000×RCF for 1 min. The supernatant was then removed. The DNA and glass particle pellet was washed once with another 20 ml of glass particle-DNA binding buffer and once with 70% ethanol. The bound DNA was then eluted with 10 ml elution buffer consisting of 0.2M sodium perchlorate and 50 mM Tris.Cl, pH 8.0, and 10 mM EDTA by agitation at room temperature for 20 minutes, and then spinning down the glass particles at 5000×RCF, 1 minute. The supernatant was transferred to a clean tube and precipitated with ethyl alcohol. DNA was digested with DNase I to generate fragments less than about 5 Kb. After extraction and precipitation, the DNA pellet was dissolved in TE buffer, pH 8.0. The ratio of $A_{260}$ to $A_{280}$ was 1.8. Using O.D. at 260 nm, the DNA concentration was calculated.

C. Preparation of RNA

Ten volumes of homogenization solution consisting of 126 g of LiCl and 360 g of Urea dissolved in 1 L of $H_2O$ was added to one gram of finely chopped liver tissue to homogenize the tissue. The mixture was then homogenized for 2 min. at 20,000 RPM. The homogenate was then incubated at 4° C. for 4 hours followed by centrifugation at 10,000×g at 4° C. for one hour. The precipitate was then dissolved in 2.5 ml of a resuspension buffer consisting of 10 mM Tris.Cl,pH 7.6; 1 mM EDTA pH 8.0; and 0.5% SDS. An equal volume of a 25:24:1 solution of phenol, chloroform and isoamyl alcohol was then added to the resuspension. The mixture was then mixed at room temperature for 20 min. followed by centrifugation at 3,000×g at room temperature for 5 min. The aqueous upper phase was then transferred to separate container and a ⅒ volume of 3M NaAc(pH5.0) was added. Precipitation was then achieved by the addition of 2 volumes of ethyl alcohol followed by a 10–15 min. incubation at −20° C. The sample was then centrifuged for 20 min. at 5,000×g at 5° C. The resulting RNA pellet was then redissolved in double distilled water. The concentration of RNA was then determined from the optical absorbance at 260 nm (1 $OD_{260}$=45 ug/ml RNA). The ratio of $A_{260}$ to $A_{280}$ was 1.95.

D. Preparation of Plasmid DNA

A plasmid-bearing bacteria strain, HB101 (Promega) transformed with the plasmid pUC 19 (GIBCO) was cultured in 500 ml LB containing 50 μg/ml Ampicillin until saturated. The culture was then centrifuged at 4000×g at 4° C. for 15 min. The bacteria pellet was resuspended in 10 ml of STET (0.1 M NaCl; 10 mM Tris.Cl, pH8.0; 1 mM EDTA, pH8.0; 5% Triton X-100) and lysed by addition of 1 ml of 10 mg/ml freshly made lysozyme. The bacteria lysate was boiled for 40 seconds and then set on ice. The lysate was then centrifuged at 12,000×g for 15 min. The supernatant was transferred and 2.5 M NaAc pH 5.2 was added to a final concentration of 0.25 M. Isopropanol was added to the supernatant (0.6×volume), mixed, set at room temperature for five minutes and then centrifuged at 12,000×g for five minutes. The supernatant was removed and the plasmid DNA pellet was washed, using 75% alcohol. After removing the alcohol, the tube was set at room temperature for ten minutes to evaporate residual alcohol. The plasmid DNA was then redissolved in 1 ml TE containing 20 μg/ml RNAse and stored at 4° C.

Sources for nucleic acid other than the above mentioned methods include bacteriophage DNA, plasmid DNA, synthetic oligonucleotides, and nucleotide precursors as well as commercial suppliers, which are readily available to one of skill in the art.

Example 2

Representative Procedures for Preparing Nucleic Acid-Containing Compounds

A. DNA-Containing Lotion

| Formula: | DNA | 0.1 g |
|---|---|---|
| | Polyethylene glycol 400 | 3.0 g |
| | Citric acid | 0.3 g |
| | Water | 79.6 ml |
| | Ethanol (95%) | 17.0 ml |

A DNA-containing lotion was prepared by slowly stirring 100 mg DNA (purified as described for Example 1A, Method I) into a solution containing 3.0 g of polyethylene glycol 400, 0.3 g of citric acid and 79.6 ml water. After the solution was mixed, 95% ethanol (17.0 ml) was added to the mixture followed by stirring at room temperature. The mixture optionally can be irriadiated under ultraviolet lamp (30 watt, 254 nm) for 10 minutes, 50 cm from the light source. Such irradiation appears to improve the protective capability of the DNA lotion. The final concentration of polyethylene glycol 400 was 3.0% (W/V) and of citric acid was 0.3% (W/V).

B. DNA-Containing Cream

DNA (0.1 g) in 3 ml TE solution, purified as described for Example 1A, Method I, was added to Formula B (see below) with stirring. Formula A (see below) was then mixed with the DNA-formula B mixture and stirred at 75° C. The mixture was then cooled to 50° C. The formulations for formulas A and B were as follows:

| Formula A | Stearic acid | 3.0 g |
|---|---|---|
| | Laureate-23 (Briji 35 ICI) | 0.35 g |
| | Ozaberite NO4 | 1.5 g |
| | Parafinn | 1.5 g |
| | Mineral oil, visc 70 | 15.0 g |
| | Petrolatum | 4.0 g |
| | Cetyl alcohol | 3.0 g |
| Formula B | GMS (glycerol monostearate) | 3.0 g |
| | TEA (a Triethanolamine) | 1.0 g |
| | Prophylene glycol | 3.0 g |
| | Methyl paraben | 0.1 g |
| | Water | 60.0 g |
| | Perfume | 0.5 g |
| Formula C | DNA or RNA in 3 ml TE buffer | 0.1 g |

Example 3

Representative Procedures for Preparing Nucleic Acid-coated Surfaces

A. DNA-Coated Plastic and Polymers

DNA can be covalently cross-linked to free hydroxyl groups in plastic resins and polymers such as poly(vinyl alcohol) and cellulose.

To activate a hydroxyl-containing resin, 100 g of resin is added to a solution, at a temperature of about 15–20° C., consisting of 50 g of cyanogen bromide (CNBr) which had been previously dissolved in 100 ml of dimethyl-formamide. The pH of the resulting resin and CNBr mixture is immediately adjusted to between 10.5 and 11.5 with 2N NaOH. The mixture is then incubated at 15–20° C. for 15 min. The treated resin is then rinsed with cold distilled water for 5 min and then rinsed in 100 ml of 10 mM $KPO_4$, pH8.0, for 3 min in order to terminate the reaction.

DNA purified as described for Example 1A is preferably digested with DNase I sufficient to generate DNA fragments smaller than about 5 kilobases. The DNA fragments are then precipitated with ethanol. The DNA pellet is subsequently dissolved in 0.1 M potassium phosphate, pH 7.5, to a final concentration of 1% by weight.

For every 100 ml DNA solution from the above step, 100 g of the treated plastic resin is added under constant agitation at a temperature of 4–10° C. The mixture is then incubated under constant agitation for 1 hour at 4–10° C. This procedure results in 95% of the CNBr activated hydroxyl groups in the plastic resin being covalently linked to DNA molecules. The reaction may be incubated longer at 4° C., e.g., up to 18 hours, to achieve higher coupling efficiencies.

The DNA coated plastic resin is separated from the remaining DNA solution by centrifugation (filtration could also be used), and then rinsed with 100 ml 0.1N NaOH for 5 min. Subsequently the DNA coated resin is further rinsed with 1000 ml 10 mM $KPO_4$ at pH8.0 for 10 min. Finally, the coated resin is rinsed with distilled water for 10 min.

Example 4

Representative Procedure for Preparing Nucleic Acid-Coated Fibers

Fiber materials to be coated with NA in this procedure include natural fibers such as cotton thread and cellulose, as well as synthetic fibers, such as nylon, and glass fibers. The procedure described below has been successfully performed with cotton thread, cellulose, nylon and glass fibers.

Each gram of dry fiber was dipped in at least 30 ml of a 0.01%–0.1% DNA or RNA solution (isolated according to the procedures described for Example 1) for 1 minute at a temperature of 10–60° C. The preferred molecular weight of DNA was between 500 bp and 5000 bp and the preferred temperature range was between 22° C. to 45° C.

The DNA or RNA-coated fiber was then dried at room temperature (for glass fiber at 100° C.), approximately 30 minutes. The dried DNA or RNA coated fibers were then irradiated under a 30 walt ultraviolet lamp (UV wavelength 254 nm) for 5 min., 20 cm from the light source.

Example 5

Representative Procedure for Preparing Nucleic Acid-Coated Matrices

A. Covalent Cross-linking of Double Stranded DNA Molecules to Free Hydroxyl Group-Containing Solid Matrices Transparent polymer plastics, glass fiber, cellulose powder or cellulose fibers which contain free-hydroxyl groups have all been satisfactorily used in the following procedure to covalently link DNA to a matrix to create an NA-containing, genetic hazard UV radiation absorbing matrix. The procedure was as follows:

(1) The solid matrices were first incubated in 0.1 N NaOH for 5 min at a rate of 500 ml of 0.1 N NaOH for every 100 $cm^2$ of matrix material. The matrices were then rinsed with at least 1200 ml per 100 $cm^2$ of matrix of distilled water for at least 7 min., until the pH of the treated matrices became neutral. The matrix material was then dehydrated in methanol.

(2) DNA purified as described for Example 1A, Method I was solubilized in TE, pH8.0, to a concentration of 0.1% (W/V). One volume of this DNA solution was then mixed with 4 volumes of a solution consisting of 50% by weight 1-cyclohexy-3-(2-morpholinoethyl) carbodiimide metho-p-toluene solfonate (CMC) in 0.2 M sodium 2-(N-morpholino)ethanesulfonate, at pH 6.0.

(3) The treated solid matrices were submerged in the above DNA-containing mixture for 16 h at 20–24° C. The DNA coated matrices were then rinsed 3 times with distilled water at 5 min. intervals, and then allowed to dry.

B. Cross-Linking Single-Stranded NA to Plastic Matrices by Ultraviolet Radiation Single-stranded DNA can be cross-linked to plastic matrices by ultraviolet radiation in the following procedure:

(1) Double-stranded DNA (prepared as described for method I, Example 1A) is first denatured into single-stranded DNA by either incubating the DNA in 0.1 M NaOH for 5 min. and adding HCl to final concentration 0.1 N and placing at room temperature 5 min. or by incubating the DNA at 98° C. for 5 min., followed by immediately dipping the solution into ice water. The solution of single-stranded DNA is then brought to a concentration of 0.1% DNA by weight.

Single-stranded DNA may also be directly obtained from single-strand DNA bacteriophages such as bacteriophage F1.

(2) Plastic matrices, prepared as described above in Example 5A, are submerged into 95% ethanol at a concentration of 500 ml of ethanol per 100 g of plastic resin. After a 5 min. incubation at room temperature, the resin is then rinsed with 1 N HCl at 500 ml HCl per 100 g of resin. The resin is then rinsed with distilled water for 7 min. and then dried at 37° C.

(3) The treated resin is then submerged into the 0.1% DNA solution for 5 min. and then allowed to dry at room temperature.

(4) To cross-link the DNA to the resin, the dried DNA-coated resin is irradiated for 15 min. under a 30 W Sylvania germicidal lamp, at a wave length range of 320–370 nm. The lamp is placed about 22 cm from the treated resins.

(5) After the cross-linking, the DNA-coated resins are rinsed with distilled water for 5 min. The DNA-coated plastic resins are then dried and stored at room temperature.

C. Cross-Linking RNA Molecules to Free Hydroxyl Group-Containing Matrices Catalyzed by Water Soluble Carbodiimide RNA molecules can be cross-linked to hydroxy group-containing matrices by water soluble carbodiimide in the following procedure:

(1) RNA molecules are purified from porcine liver tissue according to the procedure described for Example 1C, and stored in 70% ethanol at −80° C. The ethanol is removed by centrifugation immediately before using the RNA molecules.

(2) Solid matrices of the type described above for Example 5 A are washed with methanol.

(3) A 0.1% by weight RNA solution is mixed with 0.2M sodium 2-(N-morpholino) ethanesulfonate, pH6.0, at a ratio of 6:1. Carbodiimide is then added to final concentration of 7.2% W/W.

(4) 5000 $cm^2$ of solid matrices are submerged into 100 ml mixture described in step 3. The resulting mixture is then incubated for 24 hours at 22° C.

(5) Following the incubation, the RNA coated matrices are rinsed three times with distilled water, for 5 min. each rinse. The RNA coated matrices are then allowed to dry at room temperature and stored at room temperature.

Example 6

Use of DNA-Containing Lotion to Reduce Sunlight-Induced Damage to DNA

A. DNA Restriction Endonuclease Digestion Test

One of the principal ways in which genetic hazard ultraviolet radiation causes cancer is through the formation of ultraviolet light-induced pyrimidine dimers in double stranded DNA. Once formed, thymidine and cytosine dimers can lead to permanent mutations in the genetic code when the DNA copied during cellular replication. This form of mutagenesis is widely believed to be the major route through which sunlight induces both melanoma and malignant non-melanoma skin cancers.

Thus, an assay that detects the formation of ultraviolet radiation-induced thymidine dimers in double stranded DNA is desirous in assaying the efficiency of a genetic hazard ultraviolet radiation filtration system. These experiments describe such an assay. The assay described in these experiments uses restriction endonucleases which recognize and cleave specific DNA sequences containing potentially dimerizing pairs of pyrimidine bases in double stranded DNA.

The basic concept of the assay is that the restriction enzymes will cut the DNA in a specifically recognized sequence if the bases are not dimerized, whereas pyrimidine dimers will prevent cleavage by the restriction endonuclease. To assay the extent of thymidine dimerization, one assays the efficiency of enzyme cleavage. These parameters are inversely proportional. To assay the efficiency of a genetic hazard ultraviolet radiation filter, one compares the enzymatic efficiency—and hence the amount of dimerization of the bases of control samples of double stranded DNA with test samples protected by the genetic-hazard UV filter. For example, samples could include: (1) double stranded DNA that is not exposed to ultraviolet radiation (no direct sunlight); (2) double stranded DNA exposed to genetic hazard ultraviolet radiation (direct sunlight), and (3) double stranded DNA exposed to genetic hazard UV radiation (direct sunlight) and filtered with a genetic hazard ultraviolet light absorbing filter.

The following experiment describes the use of the restriction endonuclease assay in the context of evaluating the efficiency of the DNA-containing, genetic hazard ultraviolet light-absorbing lotion prepared as described above in Example 2 A. The DNA-lotion was not irradiated.

Genomic DNA of human skin fibroblast cells was purified by conventional methods (Laird, P., *Nucleic Acids Research*, 19:4293, 1991) and sealed in transparent polyvinyl chloride (PVC) bags at a concentration of 50 ug/ml in a buffer containing 10 mm Tris Cl pH 8.0. 20 mm EDTA pH 8.0. Eight such DNA containing plastic bags were used in the following experiment:

(1) Bag 1 received no exposure to sunlight.
(2) Bag 2 was exposed to sunlight with an uncoated PVC sheet interposed between the bag and the sun, from 9:00 AM to 5:00 PM, for 31 consecutive days during the month of July at an latitude of 40N.
(3) Bags 3–8 were exposed to sunlight under the identical conditions of bag 2, however for each of bags 3–8 a barrier PVC sheet was interposed between the bag and the sun; the barrier PVC sheet had been evenly coated with a given amount of a DNA-containing lotion prepared as described above in Example 2A.

The thickness of the PVC used to form the sealed bags and the PCV barrier sheets was approximately 0.1–0.2 mm. The PCV barrier sheets were placed atop the DNA-containing PCV bags. Table 1 shows the amount of DNA in ug per $cm^2$ of PVC sheet that was present on each barrier for bags 2–8.

(4) After exposure to the sunlight, all of the bags were treated via the following procedure:
 (a) The DNA solution from each bag was precipitated with ethanol. The DNA pellet was subsequently dissolved in TE buffer (10 mm Tris Cl pH 8.0, 1 mm EDTA pH 8.0). One microgram of DNA was digested with 10 units of the restriction enzymes Mse I Hpa II at 37° C. for 2 hours.
 (b) Each digest was then separated on a 0.9% agarose gel (10 cm×14 cm) run overnight (12–16 hours) at 0.5 volts/cm. Following the separation, the gels were stained 15 min with 0.5 ug/ml ethidium bromide, and rinsed twice with 10 mM $MgSo_4$ for 15 min. each time.
 (c) The efficiency of the DNA restriction digestion was determined as follows:
  (i) The gels were photographed using reverse film under ultraviolet light to produce a black and white photograph of the bands in the gel.
  (ii) The intensity (darkness due to the presence of DNA species) of each lane of the gel was then determined by a densitometer. The multiple and various sized species of DNA in the gel resulted in a DNA smear along the lane. In the presence of endonucleases, larger pieces of DNA are cut into smaller pieces, resulting in a shift in DNA-intensity of the gel from the upper half of the gel (high molecular weight species) to the lower half of the gel (low molecular weight species). If endonuclease activity is inhibited by UV-induced dimerization, this shift in intensity is reduced or lost.
  (iii) The total intensity of each lane was defined as $L_i$, where i stands for each of bags 2–8. The intensity of the lower half of the lane (i.e., low molecular weight DNA) in each lane was defined as $L_{1/2}$,i. N was defined as the percentage intensity of the lower half lane for each bag (e.g., percentage of darkness in the lane due to low molecular weight species of DNA). A decrease in the N value of each bag (decreased intensity of lower molecular weight bands) relative to the control correlates to an amount of pyrimidine dimers formed in the DNA, and is mathematically calculated as $N=L_{1/2,i}/L_i$ Compared to the no-exposure control, the N value is smaller in those DNA samples which have had some damage (dimerization) and thus cannot be fully cut by the endonuclease.

Using this method of analysis, the control, non-UV exposed DNA was calculated as $N_o=L_{1/2},o/L_o$. The protection efficiency for each experimental bag was calculated as $N_i$, where i=2,3 . . . ,8. The efficiency of each bag was then converted to a percentage of the control group via the formula: $N_i/N_o\times100\%$. The higher the N percentage, the greater the conservation of restriction sites and the less damaged the DNA, and the greater the amount of protection afforded by the composition against UV-induced genetic hazard damage. The results are summarized in Table 1 below, and indicate a high protection efficiency (e.g., approximately 90% or greater) when 50 $ug/cm^2$ or greater amounts of DNA are used as a barrier.

TABLE 1

Conservation of Restriction Sites in DNA Protected by DNA-containing Lotion

| BAG NO. | Amount of DNA on PVC sheet ($ug/cm^2$) | Conservation of MSE I sites ($N_i/N_o$) × 100% | Conservation of Hpa II sites ($N_i/N_o$) × 100% Hpa II |
|---|---|---|---|
| 2 | 0 | 3.0 | 2.1 |
| 3 | 5 | 14.9 | 11.3 |
| 4 | 15 | 27.3 | 25.1 |
| 5 | 25 | 67.2 | 59.7 |
| 6 | 50 | 91.1 | 89.2 |
| 7 | 100 | 98.4 | 97.0 |
| 8 | 150 | 99.6 | 99.1 |

B. Plasmid DNA Transformation Efficiency Test

The extent of DNA damage caused by genetic hazard ultraviolet radiation can also be measured by assaying the transformation efficiency of plasmid DNA. When plasmid DNA is exposed to sunlight, the ultraviolet light-induced structure and function damage to the DNA results in a decrease in the efficiency with which the DNA can transform a bacterial cell.

Thus, one can assay both the extent of ultraviolet light-induced damage to DNA and the efficiency of protection afforded by ultraviolet light filters, by comparing the transformation efficiency of plasmid DNA exposed to direct sunlight, with that of DNA exposed to filtered sunlight, and with that of DNA exposed to no sunlight.

In the following experiment, a 50 ug/ml solution of plasmid pBR322 DNA was placed in 8 different PVC bags and used in the following experiment:

(1) Control bag 1 received no exposure to sunlight.
(2) Control bag 2 was exposed to sunlight with a non-coated PVC sheet interposed between the bag and the sun, from 9:00 AM to 5:00 PM, for 31 consecutive days during the month of July at an altitude of 40N.
(3) Bags 3–8 were exposed to sunlight under the identical conditions of bag 2, however for each of bags 3–8 a barrier PVC sheet was interposed between the bag and the sun. The barrier PVC sheet had been evenly coated with a given amount of the DNA-containing lotion preparation described above in Example 2A. The thickness and placement of the PCV sheets was as described above for Example 6A. Table 2 shows the amount of DNA in ug per $cm^2$ of PVC that was present on the barrier for bags 2–8.
(4) After exposure to the sunlight, all of the bags were treated via the following procedure:
   (a) 10 ng of plasmid DNA from each bag was used to transform competent HB101 E. coli bacterial cells via the conventional $CaCl_2$ method (Ishiura et.al., Mol. Cell. Biol. 2::607–616, 1982).
   (b) Following transformation, the bacteria were spread on LB agar plates containing 100 ug/ml ampicillin which were then incubated overnight at 37° C.
   (c) Resulting colonies were counted and their number converted to colonies per ug plasmid DNA. The results of the experiment are shown in the Table 2 which compares the transformation efficiency of bags 2–8 with that of the non-sunlight exposed control. An amount of 50 ug/$cm^2$ or greater resulted in approximately 90% or greater colony formation, e.g. protection from UV-induced damage.

TABLE 2

Reduction in transformation efficiency related to the amount of DNA-containing lotion used to filter sunlight: Transformation Assay

| BAG NO. | Amount of DNA on PVC sheet (ug/$cm^2$) | Colony formation (percentage of non-exposed control) |
| --- | --- | --- |
| 2 | 0 | 5.1 |
| 3 | 5 | 15.3 |
| 4 | 15 | 30.0 |
| 5 | 25 | 71.4 |
| 6 | 50 | 89.7 |
| 7 | 100 | 95.9 |
| 8 | 150 | 98.5 |

Example 7

Use of DNA-Coated Plastic Sheets to Reduce Sunlight-Induced Damage to DNA

Table 3 summarizes the results of ultraviolet protection afforded by DNA-coated plastic sheets prepared as described above for Example 3B. The experiment was performed as described above for Example 6A with the amounts of DNA shown in Table 3, column 1 being the amount of DNA upon the coated plastic sheets.

TABLE 3

Conservation of Restriction Site in DNA Protected by DNA Containing Lotion

| Amount of DNA on plastic sheet (ug/$cm^2$) | Conservation of MSE I Site ($N_i:N_o \times 100$) | Conservation of Hpa II Sites ($N_i:N_o \times 100$) |
| --- | --- | --- |
| 0 | 9.5 | 7.0 |
| 15 | 29.4 | 31.2 |
| 50 | 85.2 | 89.1 |
| 150 | 98.6 | 99.6 |

Table 4 summarizes the results of ultraviolet protection afforded by DNA-coated plastic sheets prepared as described above for Example 3B. The experiment was performed as described above for Example 6B with the amounts of DNA shown in Table 4, column 1 being the amount of DNA upon the coated plastic sheets.

TABLE 4

Reduction in transformation efficiency related to the amount of DNA on DNA-coated plastic sheets used to filter sunlight: Transformation assay

| Amount of DNA on plastic sheet (ug/$cm^2$) | Colony formation (percentage of control) |
| --- | --- |
| 0 | 4.3 |
| 15 | 35.8 |
| 50 | 85.9 |
| 150 | 95.6 |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

I claim:

1. A method for protecting genetic material from ultraviolet radiation-induced damage relative to an unprotected control, the method comprising:
   placing a barrier between a source of ultraviolet radiation and a target containing ultraviolet radiation-sensitive genetic material, the barrier comprising a layer of natural polydeoxyribonucleic acid or polyribonucleic acid or a mixture thereof, in an amount ranging from 15 $\mu g/cm^2$ to about 150 $\mu g/cm^2$.

2. A method for protecting genetic material from ultraviolet radiation-induced damage relative to an un-protected control, the method comprising:
   placing a barrier between a source of ultraviolet radiation and a target containing ultraviolet radiation-sensitive genetic material, the barrier comprising natural or genetically engineered polydeoxyribonucleic acid or polyribonucleic acid or a mixture thereof,
   wherein said barrier comprises a solid or semi-solid substrate coated or impregnated with said polydeoxyribonucleic acid, polyribonucleic acid, or mixture thereof.

3. A method for protecting genetic material from ultraviolet radiation-induced damage relative to an unprotected control, the method comprising:
   applying a topical composition to an animal's skin, the topical composition comprising a natural or genetically engineered polydeoxyribonucleic acid or polyribonucleic acid or a mixture thereof, thereby forming a barrier layer between the animal's skin and a source of ultraviolet radiation, wherein protection from ultraviolet radiation-induced damage does not depend on stimulation of a tanning response.

4. The method of claim 3, wherein said topical composition is a lotion or cream.

5. The method of claim 3, wherein said applying is applying an amount sufficient to coat the animal's skin with about 15 $\mu g/cm^2$ to 150 $\mu g/cm^2$ polydeoxyribonucleic acid or polyribonucleic acid or a mixture thereof.

6. A method for protecting an animal from ultraviolet radiation-induced genetic damage relative to an unprotected control, the method comprising:

applying to an animal's skin a topical composition comprising a natural polydeoxyribonucleic acid or polyribonucleic acid or a mixture thereof in an amount sufficient to coat with about 15 $\mu g/cm^2$ to about 150 $\mu g/cm^2$ of polydeoxyribonucleic acid or polyribonucleic acid or a mixture thereof.

7. The method of claim 5, wherein said composition is a cream or lotion.

8. The method of claim 2, wherein said polydeoxyribonucleic acid or polyribonucleic acid or a mixture thereof is coated or incorporated into said barrier in an amount ranging from about 15 $\mu g/cm^2$ to about 150 $\mu g/cm^2$.

9. The method of claim 2, wherein said polydeoxyribonucleic acid or polyribonucleic acid or a mixture comprises a polymer of approximately 100 to 5000 base pairs.

10. The method of claim 2, wherein said solid or semi-solid material is formed of fibers.

11. The method of claim 10, wherein said solid or semi-solid material is formed of woven fibers.

12. A method for making a barrier to protect genetic material against ultraviolet radiation-induced damage, the method comprising the steps of:

coating or impregnating a solid or semi-solid material with a composition comprising polydeoxyribonucleic acid, polyribonucleic acid, or a mixture thereof in an amount or about 15 $\mu g/cm^2$ to about 150 $\mu g/cm^2$.

13. The method of claim 2, wherein said solid or semi-solid material is formed of plastic.

14. The method of claim 2, further comprising the step of:

irradiating said coated or impregnated surface to induce cross-linking of the polydeoxyribonucleic acid or polyribonucleic acid to the solid or semi-solid material.

15. The method of claim 2, wherein the target is human.

16. The method of claim 3 or claim 6, wherein the animal's skin is human skin.

* * * * *

UNITED STATES PATENT AND TRADEMARK OFFICE
CERTIFICATE OF CORRECTION

PATENT NO. : 6,117,846
DATED : September 12, 2000
INVENTOR(S) : Yin-Xiong Li

Page 1 of 1

It is certified that error appears in the above-identified patent and that said Letters Patent is hereby corrected as shown below:

Column 6,
Line 40, insert -- in -- before "diameter"

Column 11,
Line 33, "latitude" should read -- altitude --

Signed and Sealed this

Seventh Day of May, 2002

Attest:

Attesting Officer

JAMES E. ROGAN
Director of the United States Patent and Trademark Office